United States Patent
DiMino et al.

(10) Patent No.: US 9,775,556 B2
(45) Date of Patent: Oct. 3, 2017

(54) APPARATUS AND METHOD FOR UROFLOWMETRY

(76) Inventors: Andre' A. DiMino, Woodcliff Lake, NJ (US); Matthew Edward Drummer, Fort Lee, NJ (US); Jeffrey M. Campbell, Haworth, NJ (US); Awais Malik, New York, NY (US); Lindley Curameng, Bogota, NJ (US)

( * ) Notice: Subject to any disclaimer, the term of this patent is extended or adjusted under 35 U.S.C. 154(b) by 908 days.

(21) Appl. No.: 13/117,076

(22) Filed: May 26, 2011

(65) Prior Publication Data
US 2012/0226196 A1    Sep. 6, 2012

Related U.S. Application Data

(60) Provisional application No. 61/348,501, filed on May 26, 2010.

(51) Int. Cl.
*A61B 5/20*    (2006.01)

(52) U.S. Cl.
CPC ............... *A61B 5/208* (2013.01); *A61B 5/20* (2013.01)

(58) Field of Classification Search
CPC ...... A61B 5/208; A61B 10/007; G01G 17/04; G01N 33/493
USPC ............ 600/573, 584; 604/317, 318; 73/198
See application file for complete search history.

(56) References Cited

U.S. PATENT DOCUMENTS

| | | | | |
|---|---|---|---|---|
| 3,918,433 A | * | 11/1975 | Fuisz | A61B 10/007 600/573 |
| 4,559,649 A | * | 12/1985 | Burnett | A61B 10/007 4/144.1 |
| 4,707,864 A | * | 11/1987 | Ikematsu | A61F 5/455 4/144.3 |
| 4,988,211 A | * | 1/1991 | Barnes | G01J 5/02 374/121 |
| 5,192,428 A | * | 3/1993 | Lindstrom | A47K 11/02 210/143 |
| 5,243,712 A | * | 9/1993 | Cross | 4/144.2 |
| 5,285,532 A | * | 2/1994 | Sealy | A47K 11/12 4/144.1 |
| 5,331,548 A | * | 7/1994 | Rollema | A61B 5/205 600/561 |
| 5,722,096 A | * | 3/1998 | Pfaeffle | 4/144.1 |
| 6,000,943 A | * | 12/1999 | Dawson | C07K 14/50 4/144.1 |
| 6,021,531 A | * | 2/2000 | Kirko | 4/144.3 |
| 6,370,705 B1 | * | 4/2002 | Levinson | E03D 13/002 4/251.1 |

(Continued)

*Primary Examiner* — Sean Dougherty
(74) *Attorney, Agent, or Firm* — Leonard B. Taylor, Patent Attorney (57) ABSTRACT

The present invention generally pertains to an apparatus and a method for uroflowmetry. Uroflowmetry can generally be defined as the collection and measurement of a patient's urination for the purpose of determining urine flow data that are necessary to analyze the patient's urination by comparing the patient's urine flow data to standardized urine flow data of healthy individuals. The present invention allows medical professionals to non-invasively diagnose a patient's urination by collecting, measuring and computing urine flow data to determine if any medical conditions and symptoms that affect urine flow are present. The within invention is designed and constructed in such a manner as to allow for the collection and measurement of urination to be done quickly, easily and at a reduced cost.

7 Claims, 10 Drawing Sheets

(56) References Cited

U.S. PATENT DOCUMENTS

| | | | |
|---|---|---|---|
| 7,052,452 B2* | 5/2006 | Ulmsten et al. | 600/29 |
| 7,691,092 B2* | 4/2010 | Corcos et al. | 604/318 |
| 7,722,584 B2* | 5/2010 | Tanaka et al. | 604/317 |
| 8,048,048 B2* | 11/2011 | Kim et al. | 604/322 |
| 8,141,420 B2* | 3/2012 | Hirao | 73/198 |
| 2003/0023135 A1* | 1/2003 | Ulmsten | A61B 1/32 600/29 |
| 2003/0035302 A1* | 2/2003 | Friedman | A47K 11/00 363/1 |
| 2003/0048200 A1* | 3/2003 | Heinz | G09F 7/00 340/908 |
| 2003/0097039 A1* | 5/2003 | Besson | A61F 2/00 600/29 |
| 2004/0187199 A1* | 9/2004 | Otto | A61G 9/00 4/144.1 |
| 2004/0187200 A1* | 9/2004 | Otto | A61G 9/00 4/144.1 |
| 2004/0254737 A1* | 12/2004 | Yamamoto | G06F 19/28 702/19 |
| 2005/0040126 A1* | 2/2005 | Gaster | A61M 5/1415 211/207 |
| 2005/0256428 A1* | 11/2005 | Aundal | 600/574 |
| 2006/0253047 A1* | 11/2006 | Fox | 600/584 |
| 2007/0027459 A1* | 2/2007 | Horvath | G06F 19/3412 606/147 |
| 2007/0078784 A1* | 4/2007 | Donovan | G06F 17/30575 705/71 |
| 2008/0004576 A1* | 1/2008 | Tanaka et al. | 604/317 |
| 2008/0052810 A1* | 3/2008 | Zeeb | A47K 11/12 4/144.1 |
| 2008/0251298 A1* | 10/2008 | Kritzler | 177/45 |
| 2009/0106311 A1* | 4/2009 | Hod | G06F 17/30964 |
| 2010/0064797 A1* | 3/2010 | Hirao | 73/198 |
| 2010/0152684 A1* | 6/2010 | Kim et al. | 604/318 |
| 2010/0312136 A1* | 12/2010 | Cozzie | A61B 5/015 600/549 |
| 2012/0226196 A1* | 9/2012 | DiMino | A61B 5/208 600/584 |
| 2014/0310859 A1* | 10/2014 | Brown | A47K 11/12 4/144.1 |

* cited by examiner

APPARATUS AND METHOD FOR UROFLOWMETRY

This application claims the benefit of U.S. Provisional Application 61/348,501 filed May 26, 2010, herein incorporated by reference in Its entirety.

BACKGROUND OF THE INVENTION

1. Field of the Invention

The present invention generally pertains to an apparatus and a method for uroflowmetry. Uroflowmetry can generally be defined as the collection and measurement of a patient's urination for the purpose of determining urine flow data that are necessary to analyze the patient's urination by comparing the patient's urine flow data to standardized urine flow data of healthy individuals. The present invention allows medical professionals to non-invasively diagnose a patient's urination by collecting, measuring and computing urine flow data to determine if any medical conditions and symptoms that affect urine flow are present. The within invention is designed and constructed in such a manner as to allow for the collection and measurement of urination to be done quickly, easily and at a reduced cost. A preferred embodiment according to the present invention is easy to implement and less costly than current uroflowmetry procedures thereby allowing uroflowmetry to be administered by more medical professionals, resulting in a quicker diagnosis of a patient's medical conditions and symptoms, if any.

2. Discussion of Related Art

Uroflowmetry is a procedure that measures the volume of urine released (excreted) from the body, the speed with which the urine is excreted, and the duration of the excretion. The study of urination flow has been an accepted method for the diagnosis of diseases, conditions and symptoms of the urinary tract in patients for many years. There have been numerous methods and apparatus used in uroflowmetry to provide for the measurement and recording of the flow of urination for analysis and study by medical professionals. One of the primary purposes of uroflowmetry is for the diagnosis of prostate problems.

As a result of an increased incidence of prostate pathology the public and physicians have raised concerns regarding diagnostic techniques for the timely detection of prostate pathology. The need for improved diagnostic techniques has become more acute especially with regard to more effective screening techniques. The growing incidence in prostate pathology, especially benign prostate hyperplasia ("BPH") and prostate carcinoma, requires an improved screening apparatus and method that provides an accurate and reliable diagnostic rate for early stage detection of prostrate pathology than what was available in the past. Current concerns related to uroflowmetry within the health care system are, when is the best time to administer uroflowmetry screening, and which health care professional should perform the screening.

There are different approaches used for evaluating patients for BPH and prostate pathology. Urologists generally use case findings for BPH in symptomatic patients and uroflowmetry assists in the diagnosis of such patients. Studies have shown that if uroflowmetry indicates a decreased urine flow in a patient, there will be a definite outlet obstruction in 70% of those cases. The use of uroflowmetry by physicians is an improvement in the professional service rendered to prostrate prone patients and is recommended by various International Authorities.

Uroflowmetry enables the physician to identify patients in whom pathology has begun developing. Until recently such patients were sent home under the impression of being in perfect health due to lack of symptoms. The general physician is in an ideal position to evaluate and monitor prostate pathology with the help of uroflowmetry. Using uroflowmetry, a decrease in urine flow can be detected even before the patient will experience any symptoms. Uroflowmetry can also lead to monitoring and planning at an early stage of pathology. Middle-aged and older male patients should ideally be screened regularly for prostate-related problems like BPH. Currently most physicians who do screening, use the digital rectal examination ("DRE") as this is the only procedure available to them. Most Physicians wait for patients to demonstrate actual symptoms and then the patient is referred to an Urologist. Although DRE is an important part of physical examination, it cannot assess the median lobe, a common site of adenoma enlargement. For this and other well-documented and internationally accepted reasons, DRE has limited value as a screening procedure for prostatic obstruction. Additionally DRE is shunned by male patients and some practitioners.

International research has shown that accurate measurement of the urinary flow rate provides important and useful information that may indicate the presence of bladder outlet obstruction, and that careful examination of the patient's actual flow pattern displayed on a graph may indicate a possible etiology for an abnormal flow pattern. For this, and other well-documented reasons, uroflowmetry is currently one of the best procedures for screening male patients for prostate-related problems.

SUMMARY OF THE INVENTION

The present invention comprises a method and apparatus for measuring urine flow in volume per unit of time and providing an electronic and printed representation of such flow for diagnostic purposes by a physician or medical professional. The electronic and printed representation is in the form of a graph showing the actual volume voided over a specific time period. Statistics like maximum flow rate, average flow rate, total volume voided, maximum flow time and time taken to void a measured volume are indicated on the electronic and printed output.

An aspect according to the present invention preferably comprises a self-contained electro-mechanical device that is easy to use with visual results that can be interpreted by any physician or medical professional. Because urinary flow rate is the product of detrusor action against outlet resistance, a variation from the normal flow rate might reflect dysfunction from either. The normal flow rate can be up to 25 ml/s in males and 30 ml/s in females, provided the bladder is full (total volume not less than 120-150 ml). A flow rate of less than 15 ml/s is regarded as abnormal and the statistics provided by the apparatus will then assist the medical practitioner to determine the cause and action to be taken.

In another aspect according to the present invention the apparatus preferably would be self contained and simple for the patient to use in the privacy of a restroom without the necessity of oversight by the physician or assistant.

Another preferred aspect according to the present invention further comprises a disposable funnel into which the patient would urinate. The disposable funnel would direct urine into a disposable collection-cup. The disposable collection-cup would be held in a fixture that is connected to an electro-mechanical precision force sensor. The foregoing would all be contained in a portable, light and easy to move apparatus.

Another aspect according to the present invention preferably comprises a apparatus that would produce a graph of the measurement of the change in flow of urine against time in form of a printout, an electronic file or both. The printout or electronic file would be delivered through a printer or computer that is connected to the apparatus either by wire or wirelessly such that the apparatus can transmit a printout or electronic file through a wireless connection such as Bluetooth or any other accepted wireless protocol including, but not limited to 802.11 (g), (b), (n) or other protocols used for the purpose of transmitting data.

The term "low surface energy coating" as used within this application means coatings such as polyethylene, acrylic, urethane, a polyethylene compound, an acrylic compound, a urethane compound, modified polyethylene, modified acrylic, modified urethane, polyethylene with silicon, acrylic with silicon, urethane with silicon, any combinations of the above, or any other combinations of chemicals that result in the tendency to repel, rather than attract adhesives. As used within this application low surface energy means preventing an adhesive from sufficiently wetting a surface wherein wetting refers to the ability of a liquid maintain contact with a solid surface.

The above and yet other embodiments, objects and advantages of the present invention will become apparent from the herein set forth Description of the Drawings and Detailed Description of the Invention.

BRIEF DESCRIPTION OF THE DRAWINGS

Apparatus and methods that are particular embodiments of the invention will now be described, by way of example, with reference to the accompanying diagrammatic drawings.

DETAILED DESCRIPTION OF THE INVENTION

Figure 1:
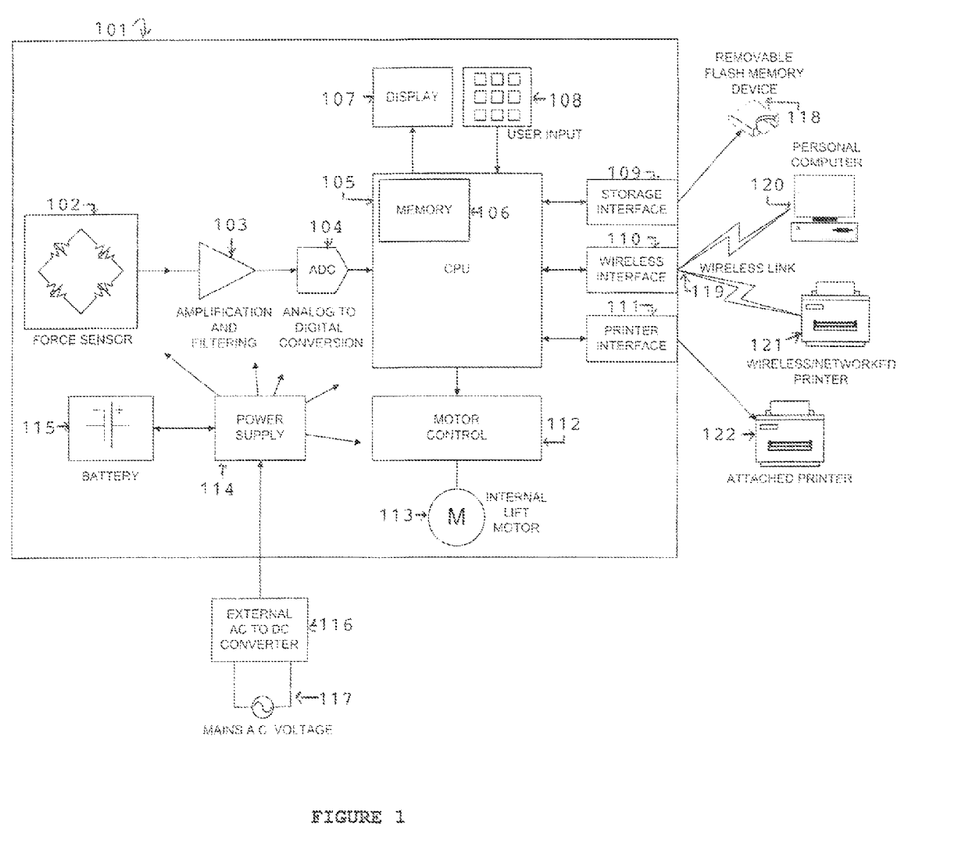
FIG. 1 illustrates a schematic of an uroflometry apparatus according to a preferred embodiment of the present invention.

Referring to FIG. 1 which illustrates a schematic of an uroflometry apparatus, a main unit 101 comprises a power source such as an external AC to DC converter 116 that converts a line voltage 117 to a DC supply voltage or an internal battery 115 that can be either replaceable or rechargeable. Preferably an internal power supply 114 mitigates switching between the external AC to DC converter 116 and the internal battery 115. The internal power supply 114 monitors and controls the charging of the internal battery 115. The internal power supply 114 regulates and supplies working voltages to all internal circuits.

A display 107 shows the status of the uroflowmetry apparatus in text, a graphic display or both. The status can include but is not limited to, measurement status, printout settings, connection settings and error messages. An end user can change some apparatus settings using user input keys 108.

The height of the apparatus can be adjusted by the user to maximize user comfort. Adjusting the height of the apparatus will correspondingly adjust a disposable funnel and a disposable collection cup that the funnel drains into. The user input keys 108 signals a Central Processing Unit 105 to adjust the height of the apparatus and its disposable funnel and disposable collection cup.

The Central Processing Unit 105 then instructs a motor control 112 circuit to move a motor 113 up or down thereby adjusting the height of the disposable funnel and the disposable collection cup.

A force sensor 102 is mounted to mechanical linkage that holds a disposable collection cup. As the collection cup fills with urine the force sensor outputs an electronic signal that changes in proportion to the weight of the urine in the collection cup. The electronic output of the force sensor 102 can be amplified and filtered 103 before conversion to a digital value via an analog to digital converter 104. Filtering can be implemented digitally as a function of the Central Processing Unit 105. A resolution of the analog to digital converter 104 is no less than 12 bit.

Each conversion is representative of the weight of urine in the collection cup. Since the apparatus is intended to be used in a stationary environment, weight is treated as mass. Taking into account the fact that urine has a uniform density, close to that of water, the conversions are representative of the volume of urine in the collection cup. A series of conversions carried out at known times preferably at a rate of 5 times per second, are then stored on the internal memory 106. The time of analog to digital conversion is much shorter than the interval between conversions and less than the rate of volume increase in the collection cup such that the conversion can be treated as nearly instantaneous. Therefore the difference between consecutive conversions over a time interval between conversions yields the average flow or, rate of change in volume, of urine in the collection cup. Using many conversions, a flow vs. time profile can then be calculated.

The flow time profile in an internal memory 106 is then transmitted to one or more output devices. Output device options are a direct printout from an attached printer 122 through a printer interface 111, storage on a removable flash memory device 118, or by using a wireless interface 110 connected to a wireless link 119, output can be stored on a personal computer 120 or directed to print using a wireless/networked printer 121.

Figure 2:
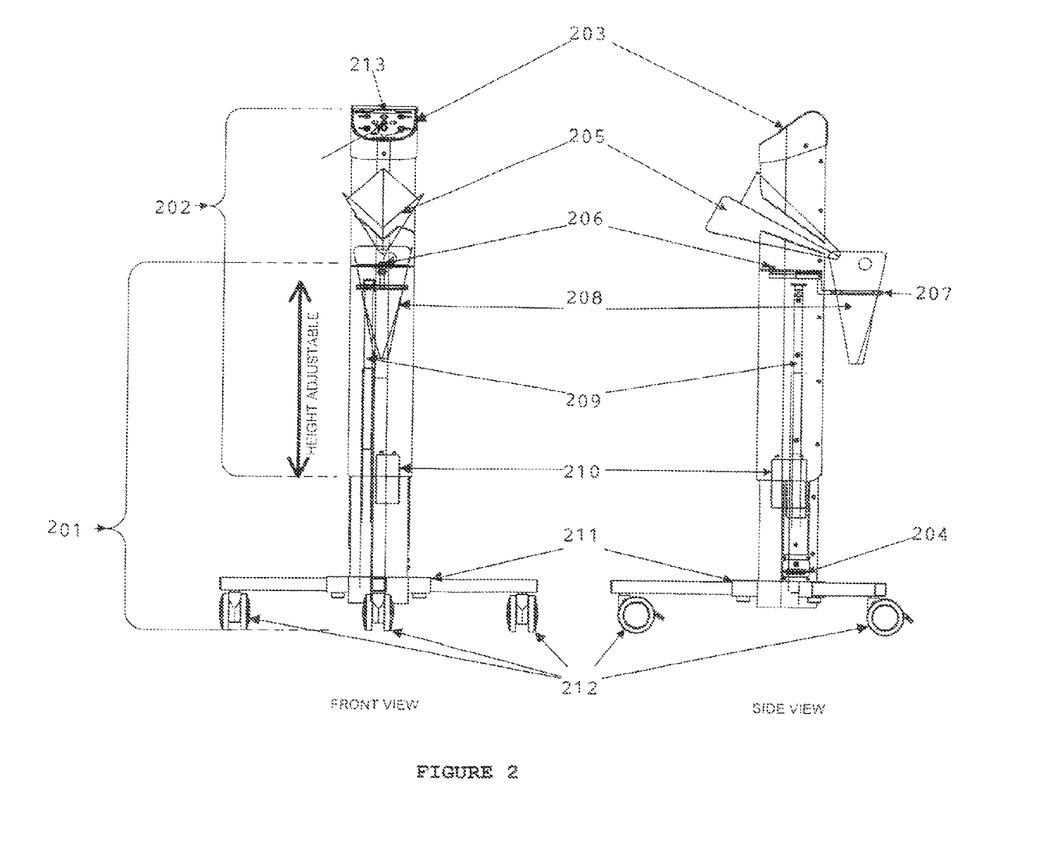
FIG. 2 illustrates an uroflowmetry apparatus according to a preferred embodiment of the present invention.

Referring to FIG. 2 which illustrates an uroflowmetry apparatus, the uroflometry apparatus comprises three major sections: an upper housing 202, lower housing 201 and a supportive base 211. Locking caster wheels 212 can be attached to the supportive base 211 to allow ease of movement.

The upper housing 202 encloses a majority of its electronic components. A control panel 203 located at a top area or at an area that supplies convenient access for the patient contains a display 213 and user input keys 214. Preferably a disposable urine funnel 205 preferably treated with a water resistant coating to reduce friction thereby making measurements more accurate and disposable collection cup 208; and internal force sensor/strain gauge 206 are supported in the upper housing 202.

A collection cup perch 207 is connected to the internal force sensor/strain gauge 206. The collection cup perch 207 can be a ring or platform that supports a urine collection cup 207 and directs a force to the force sensor 206 for measurement however other collection cup supports can be used.

The upper housing 202 and lower housing 201 telescope around each other. The upper housing 202 can move up or down relative to the lower housing 201. This adjusts the height of the urine funnel 207 to an optimal height for end user comfort. Movement of the upper housing 202 is driven by an internal height adjustment mechanism 209. The height adjustment mechanism is driven from an internal lift motor 210 however a manual adjustment mechanism can be configured.

An attached printer and power input are connected to a uroflometry apparatus by access panel 204. The access panel 204 can be located on any of the three major sections that supplies convenient access and is safe.

Figure 3:
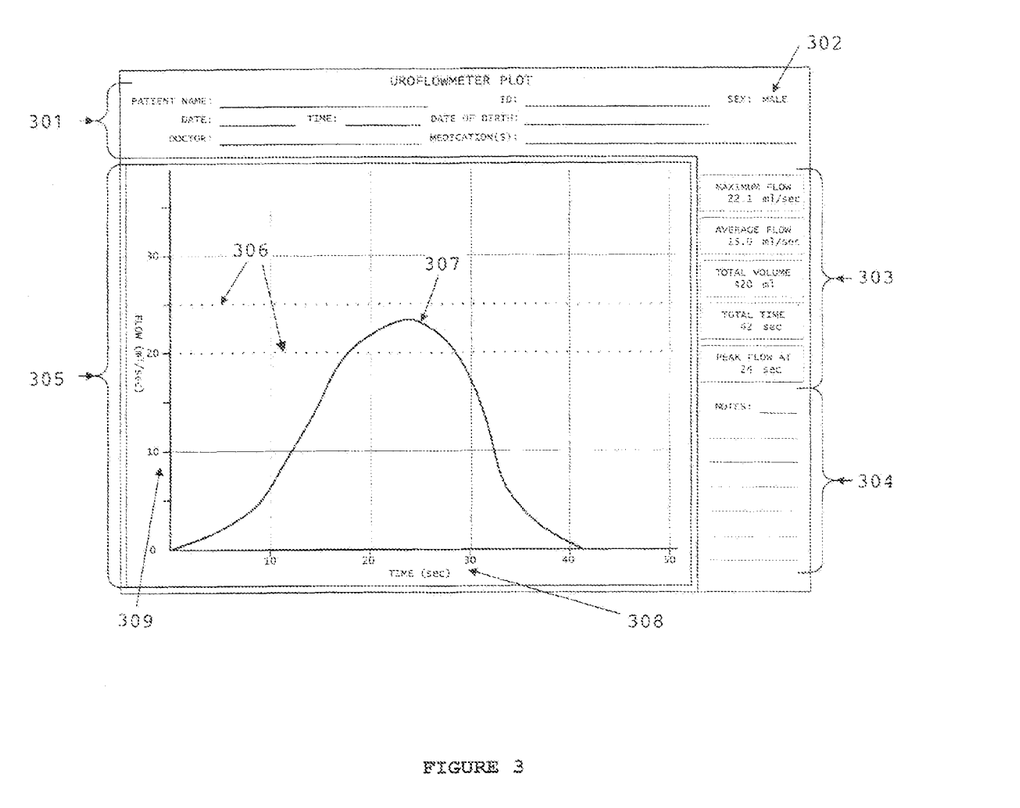
FIG. 3 illustrates an uroflometry apparatus output reference example, displaying major information components that are common to all output formats according to a preferred embodiment of the present invention.

Referring to FIG. 3 which illustrates an uroflometry apparatus output reference example, displaying major information components that are common to all output formats. The apparatus output can take the form of a printout, data file, and/or graphic display.

Patient information 301 is either in by handwriting directly onto a printout after measurement or digitally entered using user input keys 214 (see FIG. 2 above) and/or using a personal computer 120 interface (see FIG. 1 above). A patient sex 302 is a parameter that is entered from the user input keys 214 (see FIG. 2 above) and/or a personal computer 120 interface (see FIG. 1 above) prior to the measurement process.

The patient's sex determines at what flow the peak flow reference lines 306 appear on the output. The Operator can choose Male, Female, or None. Selecting a Male setting places the reference lines 306 at the upper and lower urine flow limits for average male flow. Selecting a Female setting places the reference lines 306 at the upper and lower urine flow limits for average female flow. Selecting a None setting will not display reference lines. Calculated measurements 303 are displayed. The measurements include but are not limited to Maximum Flow, Average Flow, Total Volume, Total Test Time, and the Time to Peak Flow.

A data display 305 shows the measurement results 307 that represents the flow 309 as a function of Time 308. The units of measure can be in any Metric and or English standard system.

Figure 4A:
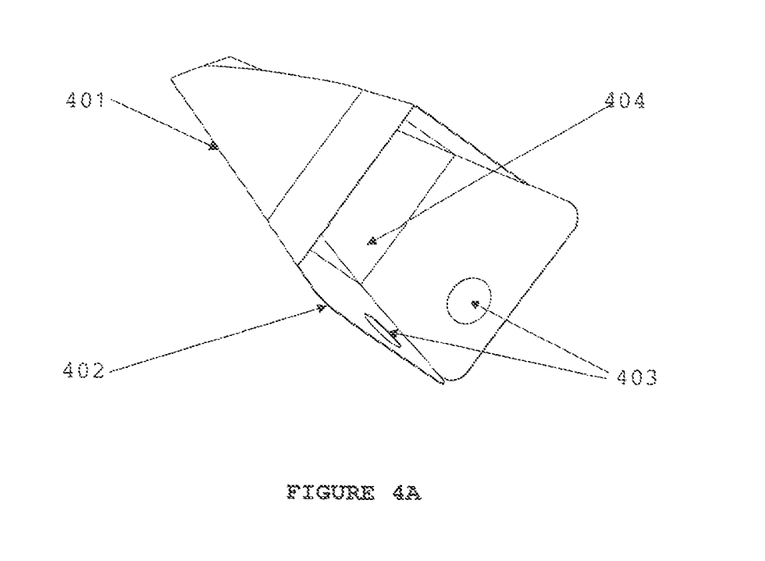
FIGS. 4A and 4B illustrate a collapsible disposable collection cup that is incorporated into an uroflometry apparatus according to a preferred embodiment of the present invention.
Figure 4B:
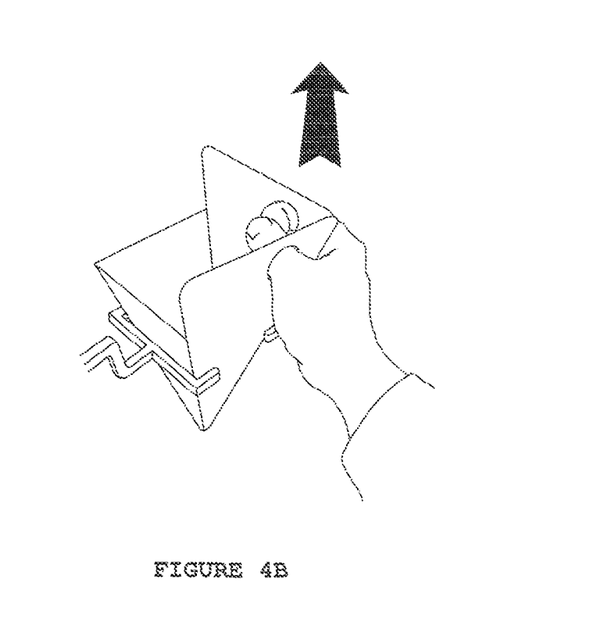

FIGS. 4A and 4B illustrate a collapsible disposable collection cup that is incorporated into an uroflometry apparatus FIG. 4A illustrates a collapsible collection cup in its open configuration. The collection cup comprises an exterior surface 401 on which branding, instructions, and any required symbols can be printed. The collection cup further comprises two adjacent tabs that extend above other top tabs of the collection cup to form a collection cup handle 402. A grasper 403 is incorporated into the collection cup handle 402. The grasper 403 allows a user to easily lift the collection cup after use while preventing the collapse of the collection cup. The collection cup can be lifted by placing a thumb and fore finger through the grasper 403, and exerting an upward motion. FIG. 4B illustrates a user's hand removing a collection cup. The inside of the collection cup 404 can be treated with a water resistant coating to reduce friction but other coatings can be used such as color changing chemicals that either indicate that the collection cup was used, or to perform a simple diagnostic function, such as pH testing, testing for the presence of blood, glucose or other commonly performed urine analysis tests.

Figure 5:
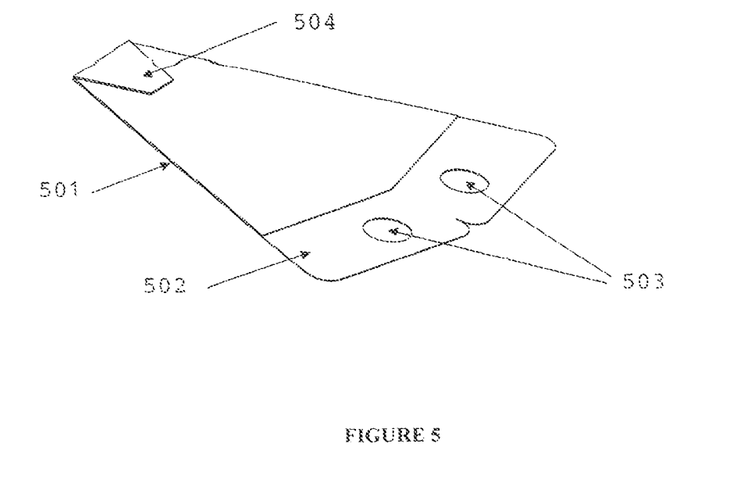
FIG. 5 illustrates a disposable collection cup in a collapsed configuration according to a preferred embodiment of the present invention.

FIG. 5 illustrates a disposable collection cup in a collapsed configuration. In the collapsed configuration the body 501 and the handle 502 having graspers 503 of the collection cup is nearly flat, enabling large quantities of the collection cup to be efficiently warehoused and shipped. To seal a bottom of the collection cup, a tip 504 of the collection cup is folded over and sealed with an adhesive preferably an adhesive that is water resistant.

Figure 6:
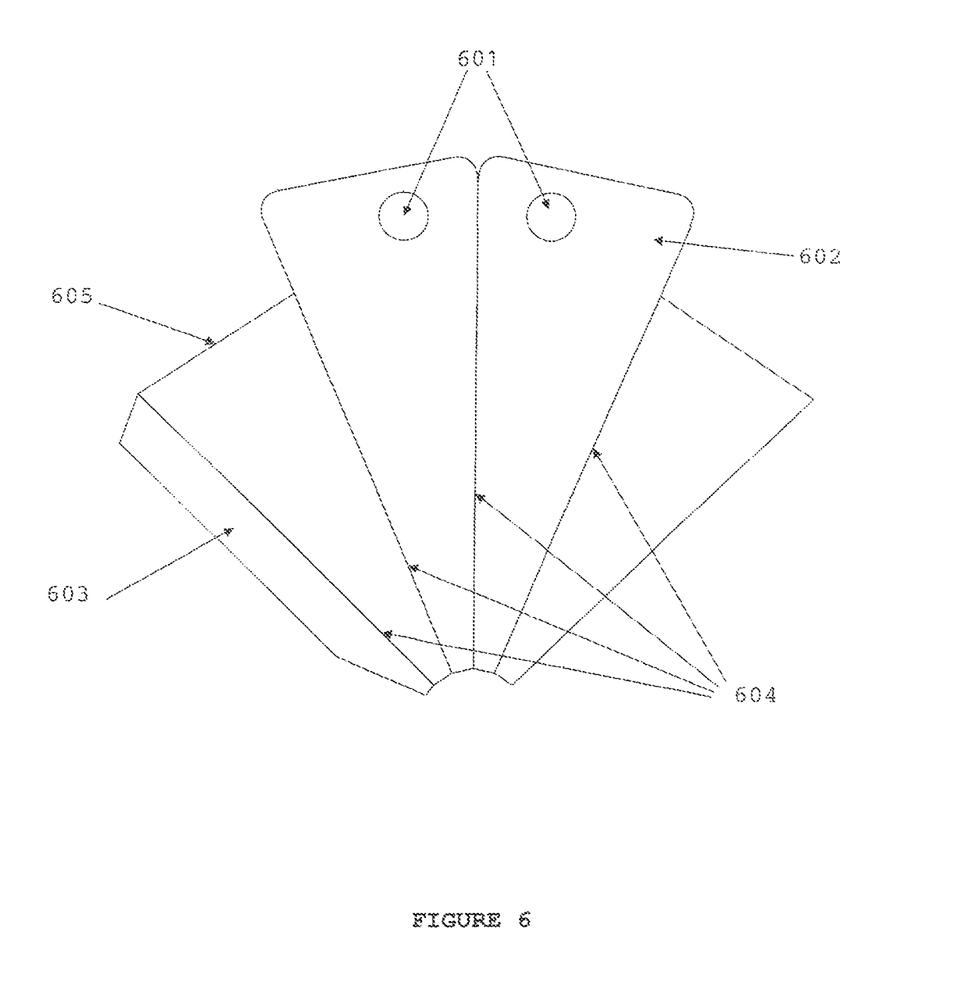
FIG. 6 illustrates the construction of a disposable collection cup from a single piece of substrate according to preferred embodiment of the present invention.

FIG. 6 illustrates the construction of a disposable collection cup from a single piece of substrate. The grasper holes 601 are shown here in the elongated portion 602 of the collection cup flat template 605. A small tab 603 is coated with a water resistant adhesive such that when folded to contact an opposing wall the small tab 603 will adhere to the opposing wall to form the four major sides of the collection cup. Scoring the seams 604 at the points where the substrate is to be folded enable accurate manufacture and ease of use. Once the collection cup is formed, the lower end is folded up and glued in order to seal the end.

Figure 7:
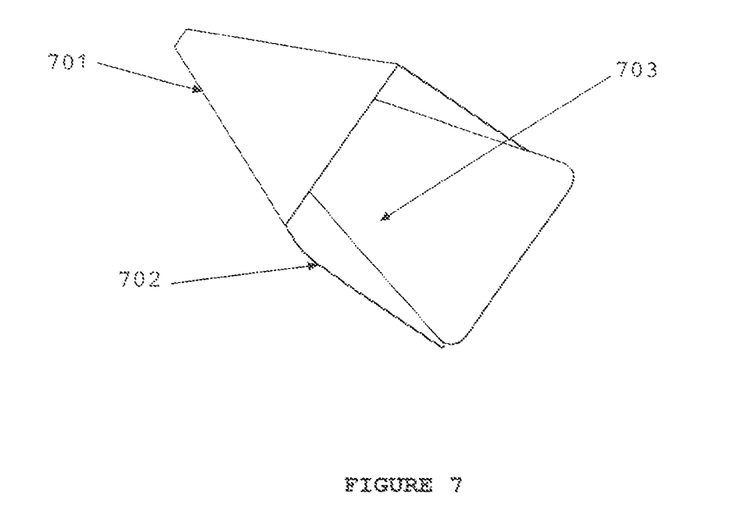
FIG. 7 illustrates a disposable funnel in an open configuration according to a preferred embodiment of the present invention.

FIG. 7 illustrates a disposable funnel in an open configuration. An outside of the funnel 701 is where branding, instructions, and any required symbols are printed. Two adjacent elongated tabs 702 of the funnel 701 are extended above the top of the large inside opening 703 to form tabs. During operation the funnel is mounted in an uroflowmetry apparatus in a nearly horizontal position with a slight downgrade (less than 45 degrees from the horizontal) from the wide to narrow end. This position functions as a buffer to channel the urine from the user to the funnel to the collection cup. The elongated tabs 702 on the wide end of the funnel 701 are placed in the down position to catch and prevent any bodily fluids from contaminating the uroflowmetry apparatus. The inside 703 of the funnel 701 is coated with a water resistant low surface energy coating but other low surface energy coatings can be used. A low surface energy coating reduces friction and minimizes any effects the funnel 701 may have on flow of urine. The inside 703 of the funnel 701 can also be coated with color changing chemicals in strategic areas that either indicate that the funnel was used or to perform a simple diagnostic function, such as pH testing, testing for the presence of blood, glucose, and other urine analysis.

Figure 8:
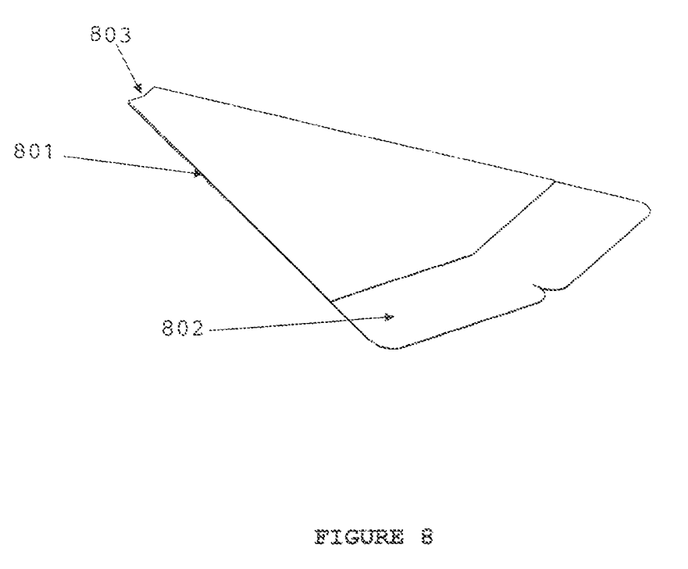
FIG. 8 illustrates a disposable funnel in the collapsed configuration according to a preferred embodiment of the present invention.

FIG. 6 illustrates a disposable funnel 801 having a funnel handle 802 and a smaller funnel tip opening 803 in the collapsed configuration. In the collapsed configuration the funnel 801 is nearly flat, enabling large quantities of the funnel 801 to be cost-effectively and efficiently warehoused and shipped.

Figure 9:
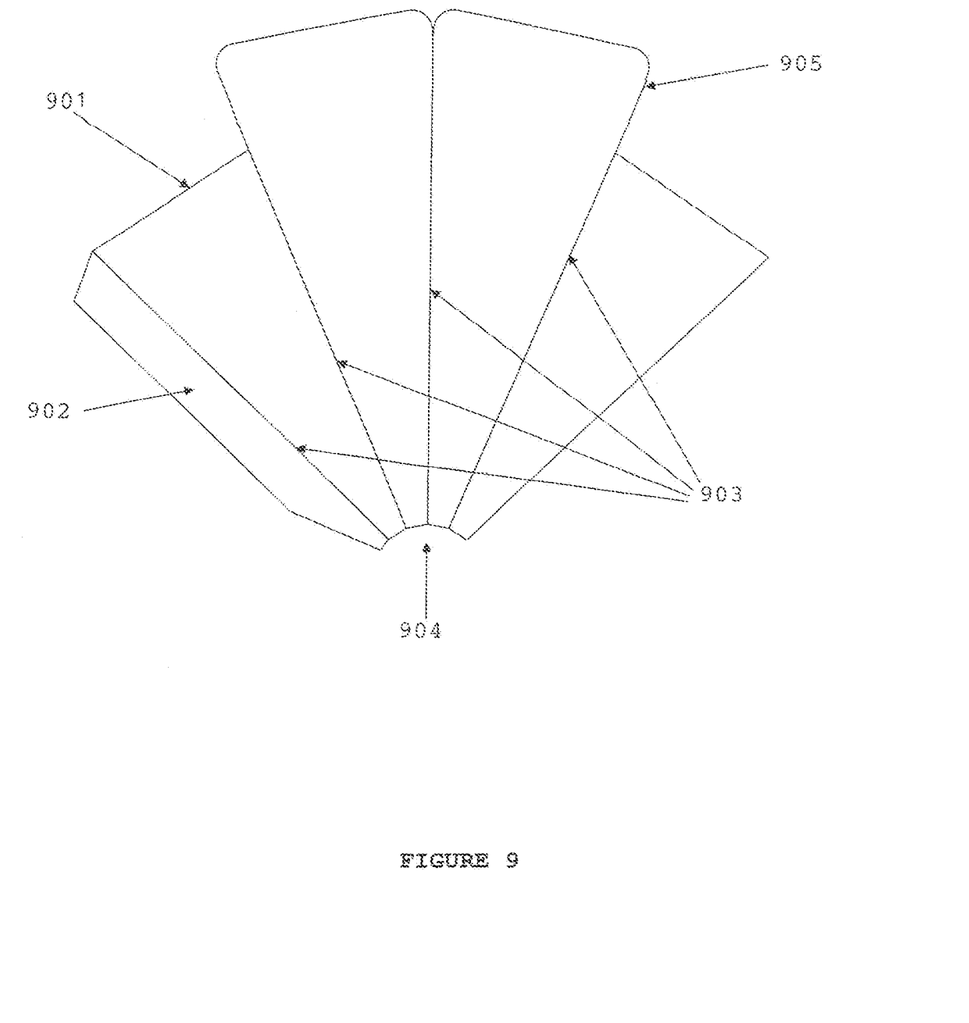
FIG. 9 illustrates construction of a disposable funnel from a single piece of substrate according to a preferred embodiment of the present invention.

FIG. 9 illustrates construction of a disposable funnel 901 from a single piece of substrate. A small tab 902 is coated with an adhesive preferably water resistant, such that the small tab 902 adheres to an opposing wall to form the four major sides of the funnel. Scoring the seams 903 at the points where the substrate is to be folded enable accurate manufacture and ease of use. The funnel tip opening 904 is formed when the small tab 902 adheres to an opposing wall. Elongated sides 905 of the funnel 901 can be used as a handle to position the funnel 901 into the uroflowmetry apparatus.

Figure 10:
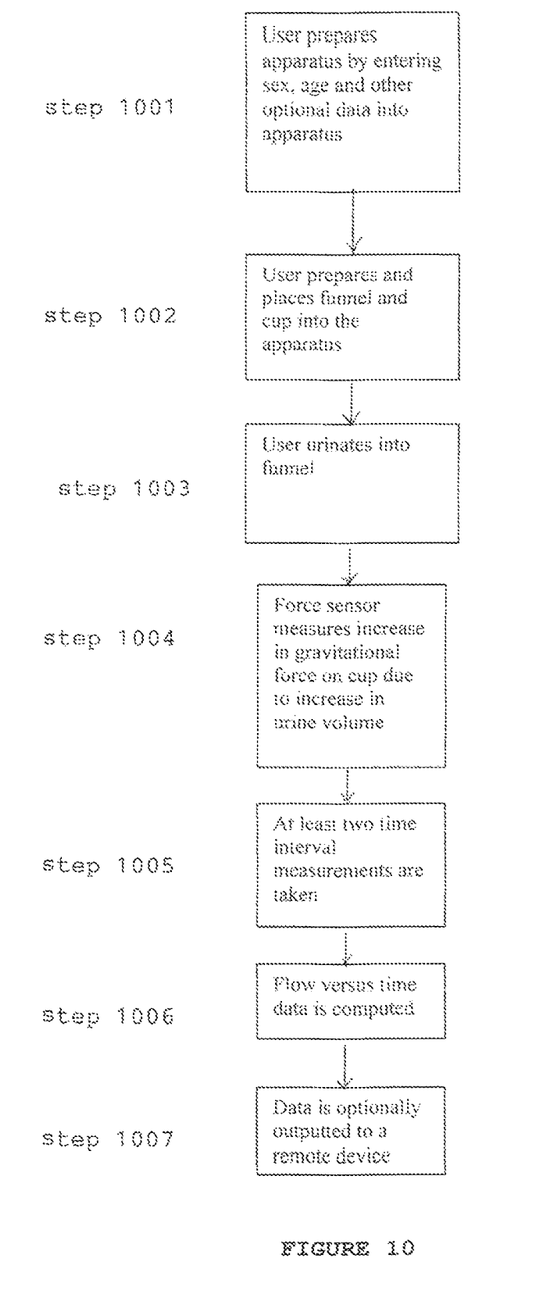
FIG. 10 illustrates a method of uroflowmetry according to a preferred embodiment of the present invention.

Referring to FIG. 10, an end user prepares an uroflowmetry apparatus for use by adjusting the height of an uroflowmetry apparatus for ease of use and comfort and entering relevant data such as name, date of birth, sex, doctor name and medications being used 1001, however not all user data is required and the uroflowmetry apparatus can modified to accept other data. The uroflowmetry apparatus can be used in a lavatory or private office for added comfort and privacy of the user.

A collapsed disposable funnel and disposable cup are assembled by folding their respective substrates at the seams and adhering the small tabs of each to their respective opposing walls. Once the Funnel and cup are assembled, the funnel is positioned into a funnel holder and the cup is positioned to into a cup platform 1002. The uroflowmetry apparatus is now ready for use. As the end user urinates into the funnel, urine passes through the funnel and is collected by the collection cup 1003. The internal electronics of the uroflowmetry apparatus instigates and records measurements as the end user urinates. A force sensor is mechanically attached to the disposable urine collection cup. The force sensor can be any electro-mechanical device that converts force to an electronic output. Examples of a force sensor include, but are not limited to, two or four element strain gauges, magnetic solenoids, electrostatic, capacitive, electrorestrictive, magnetorestrictive, piezoelectric, optical devices and other similar devices. The force sensor measures the increase in gravitational force on the collection cup due to the increase in volume in urine 1004. At least two measurements are taken at a known time interval to determine the average flow during that time interval 1005. A series of these measurements determines the change in urine flow as a function of time.

The flow vs. time data is computed and stored on internal flash memory 1006 and can be outputted as a graphic and/or data file to various wired and wireless remote output devices 1007.

It is intended that any other advantages and objects of the present invention that become apparent or obvious from the detailed description, drawings or illustrations contained herein are within the scope of the present invention.

Having described embodiments for an apparatus and a method for uroflowmetry it is noted that modifications and variations can be made by persons skilled in the art in light of the above teachings. It is therefore to be understood that changes may be made in the particular embodiments of the invention disclosed which are within the scope and spirit of the invention as defined by the appended embodiments, objects and descriptions.

What is claimed is:

1. A method for uroflowmetry comprising:
   entering patient data into a data entry area of a uroflowmetry device with user input keys, wherein the patient data includes name, date of birth and sex;
   positioning a cup onto a cup support of the uroflowmetry device, wherein the cup support includes a force sensor;
   positioning a funnel into a funnel support in a body of the uroflowmetry device to drain into the cup;
   adjusting the distance of the funnel from the ground with an adjustment mechanism of the uroflowmetry device in response to a signal from user input keys; urinating into the funnel such that the urine flows through the funnel into the cup thereby activating the force sensor;
   measuring the increase in gravitational force on the cup by the force sensor at a first time interval due to the increase in volume of urine by converting the gravitational force obtained by the force sensor into a first electronic output;
   measuring the increase in gravitational force on the cup by the force sensor at a second time interval due to the increase in volume of urine by converting the additional gravitational force obtained by the force sensor into a second electronic output; and
   computing flow versus time urination data using a central processing unit that is electronically connected to the force sensor and digital memory, processing the first electronic output received from the force sensor, the second electronic output received from the force sensor and flow versus time equations previously stored in the digital memory,
   wherein the funnel includes a narrow end, a funnel body, a wide end, at least two scored seams originating at the narrow end and extending along the funnel body to the wide end and two elongated tabs adjacent to one of the at least two scored seams at the wide end which protrude above a top of the wide end,
   wherein the funnel body is positioned substantially horizontal to the funnel support in the body of the uroflowmetry device such that the funnel has a downgrade which is less than 45 degrees from the horizontal and slopes downward front the wide end of the funnel to the narrow end, and
   wherein the funnel support is formed from the body of the uroflowmetry device and has an internal shape that is substantially the same as an external shape of the funnel so than when the funnel is positioned into the funnel support the adjacent elongated tabs on the wide end of the funnel are positioned downward relative to the ground to catch and prevent bodily fluids from contaminating the uroflowmetry device.

2. The method of claim 1, wherein the flow versus time urination data include at least one of maximum flow, average flow, total volume, total test time, and the time to peak flow.

3. The method of claim 1, wherein an interior of the funnel is coated with a friction reducing substance, a pH testing substance and a blood presence indicator.

4. The method of claim 1, further comprising:
   displaying the flow versus time urination data and patient data in the display area of the uroflowmetry device;
   displaying an upper urine flow limit and a lower urine flow limit in the display area of the uroflowmetry device for a male when the sex entered is male; and
   displaying the upper urine flow limit and the lower urine flow limit in the display area of the uroflowmetry device for a female when the sex entered is female.

5. The method of claim 1, wherein the body of the uroflowmetry device includes:
   an upper portion having the display area, the data entry area and funnel insertion area; and a lower portion connected to a base such that the base supports the body in a vertical position relative to the ground, and the lower portion has a narrower perimeter relative to an inside perimeter of the upper portion such that the lower portion is positioned within the upper portion, the lower portion including the adjusting mechanism connected to the upper portion on one end and the lower portion on the other end and able to pull the upper portion closer toward the adjusting mechanism or push the upper portion away from the adjusting mechanism.

6. The method of claim 1, wherein the force sensor includes at least one of magnetic solenoids, two element strain gauges, four element strain gauges, electrostatic devices, capacitive devices, electrorestrictive devices, magnetorestrictive devices, piezoelectric devices, optical devices.

7. The method of claim 1, wherein the funnel is constructed from at least one of plastic having a low surface energy coating, paper having a low surface energy coating, cardboard having a low surface energy coating and rubber having a low surface energy coating, and has a flat profile when not used and a funnel shape obtained by folding at the scored seams when in use.

\* \* \* \* \*